United States Patent [19]

Jacobsen et al.

[11] 4,190,047

[45] Feb. 26, 1980

[54] METHOD AND APPARATUS FOR PERITONEAL DIALYSIS

[75] Inventors: Stephen C. Jacobsen; Robert L. Stephen; David F. Knutti; Carl Kablitz, all of Salt Lake City, Utah

[73] Assignee: University of Utah, Salt Lake City, Utah

[21] Appl. No.: 828,073

[22] Filed: Aug. 26, 1977

[51] Int. Cl.² .................... A61M 5/00; A61M 1/03
[52] U.S. Cl. ........................... 128/213 A; 210/23 R
[58] Field of Search ........... 128/213 R, 213 A, 214 R, 128/227; 210/22 A, 23 R, 321 B

[56] References Cited

U.S. PATENT DOCUMENTS

| | | | |
|---|---|---|---|
| 3,520,298 | 7/1970 | Lange | 128/213 A |
| 3,783,866 | 1/1974 | Tirkkonen | 128/213 A |
| 3,802,432 | 4/1974 | Djerassi | 128/214 R |
| 3,825,493 | 7/1974 | Brown et al. | 128/213 A X |
| 3,872,863 | 3/1975 | Lasker et al. | 128/213 A |
| 3,939,069 | 2/1976 | Granger et al. | 210/321 B X |
| 4,081,372 | 3/1978 | Atkin et al. | 128/214 R X |

OTHER PUBLICATIONS

Boen et al., Trans. Amer. Soc. Artif. Inter. Orgs., vol. VIII, 1962, pp. 256-262.

Shinaberger et al., Trans. Amer. Soc. Artific. Inter. Organs., vol. XI, 1965, pp. 76-81.

*Primary Examiner*—Dalton L. Truluck

[57] ABSTRACT

Metabolic waste products from the blood of a patient are removed by pumping dialysis solution into the peritoneal cavity of the patient, and then (a) removing a portion of the dialysis solution from the peritoneal cavity which portion may vary from 1 percent to 90 percent of the total amount of dialysis solution administered to the peritoneal cavity and, (b) "cleaning" (removing metabolic waste products) this solution either through a dialyzer or by means of sorbent modules and then returning this same (cleansed) fluid into the peritoneal cavity. This cycle is repeated again and again until the desired amount of metabolic waste products are removed.

Another subcutaneous peritoneal catheter is shown in the U.S. patent application Ser. No. 594,374 filed July 9, 1975, since abandoned in favor of Continuation-in-part Application Ser. No. 768,520 filed Feb. 14, 1977. This application discloses a dual catheter, two needle system devoted to cross-flow peritoneal dialysis, whereas the present invention is directed to single catheter and single needle system operating on a push-pull principle.

11 Claims, 6 Drawing Figures

METHOD AND APPARATUS FOR PERITONEAL DIALYSIS

BACKGROUND OF THE INVENTION

Peritoneal dialysis is utilized for removal of toxic factors from the bloodstream in patients who have been poisoned, or who suffer from end stage kidney disease and thus become uremic.

In the prior art techniques for peritoneal dialysis, sterile entry is obtained to the peritoneal cavity, after which a specified volume of peritoneal dialysis solution is inserted. The dialysis solution is allowed to remain in the patient for a predetermined length of time, after which it is pumped out and this cycle is repeated many times.

In accordance with this invention, it has been determined that this type of administration of peritoneal dialysis solution does not yield the optimum result in terms of dialysis effeciency because for a significant period of time i.e. the inflow and outflow period of time, the peritoneum is not fully in contact with dialysis solution. Also, as the dialysis solution stands in flowless, quiescent condition in the peritoneum in the intestinal wall can form where the solution is largely saturated with the toxic factors, which slows down the dialysis process.

It is of course most desirable to accelerate the peritoneal dialysis process to a maximum rate of dialysance, particularly since it is generally slower than hemodialysis.

The method and apparatus of this invention are capable of providing an increase in the overall efficiency of the peritoneal dialysis process for improved dialysis process for improved dialysis, while taking advantage of the known advantages of peritoneal dialysis, for example, the fact that it is not neccessary to remove blood from the body in an extracorporeal circuit in peritoneal dialysis.

DESCRIPTION OF THE INVENTION

In accordance with this invention, metabolic waste products are removed from the blood of a patient by pumping dialysis solution into the peritoneal cavity of the patient. In accordance with this invention, the following steps are provided: (a) removing a portion of the dialysis solution from the peritoneal cavity, which portion may vary from 1 percent to 90 percent of the total amount of dialysis solution administered to said peritoneal cavity; (b) replacing said portion with "cleansed" dialysis solution, and sequentially repeating steps (a) and (b) until the desired amount of metabolic waste products have been removed from the patient.

The dialysis process of this invention has singular advantages over the prior art process of insertion of a charge of dialysis solution allowing it to remain quiescently in the peritoneal cavity for a period of time, and then removing the dialysis solution so inserted. In the invention of this application, dialysis solution is initially charged to the peritoneal cavity, and then, preferably on a continuous process basis, a portion of the dialysis solution so inserted into the peritoneal cavity is sequentially drained, cleansed and reinfused. A preferred volume of the portion so exchanged ranges from 30 to 60 percent of the initial volume of dialysis solution placed in the peritoneal cavity.

Preferably, as soon as the desired volume has been removed, a similar volume of cleansed dialysis solution is added until the initial volume in the peritoneal cavity is achieved.

Immediately following this, preferably, the fraction of dialysis solution is again drained from the peritoneal cavity until, for example, 40 percent of the total volume has been so drained, at which time cleansed dialysis solution is once again replaced to the peritoneal cavity to make up the total 100 percent volume again.

This process continues for preferably at least 50 to 150 partial exchanges, or more if desired, providing an intrinsically increased efficiency of dialysis.

While not wishing to be limited to any theory for why the dialysis process is more efficient, it is believed that the very fact that dialysis solution is moving most of the time in the peritoneal cavity because of the frequent draining and refilling thereof, causes the breakdown of saturated boundary layers of dialysis solution adjacent the peritoneum and intestinal wall. This permits more efficient utilization of the dialysis solution. Also, the regular, intermittent replacement of part of the dialysis solution with cleansed dialysis solution is helpful for dialysis efficiency. Finally, examination of the two processes will show that it is possible for a greater area of the peritoneum to be exposed to dialysis solution for a longer time during the dialysis process of this invention, to raise the average volume of dialysis solution in the peritoneum over time, when compared with the prior art process.

The total amount of dialysis solution which may be initially administered to an adult patient may be, for example, from 1,000 ml. to 2,500 ml., depending upon the size of the patient and other factors. This amount of dialysis solution is called the intraperitoneal volume. (IPV)

The fraction of dialysis solution which may be removed and replaced from the IPV may range, for example, from 500 to 1,500 ml. once again depending upon the individual patient, this amount being called the stroke volume. (SV)

The inflow and outflow rates of dialysis solution may be on the order of 350 ml. per minute, or otherwise as desired.

In one large male patient, who underwent peritoneal dialysis in accordance with this invention, IPV of 2,000 ml. and 2,500 ml. respectively were used on various occasions. The stroke volumes in various peritoneal dialysis sessions were varied between 500 ml., 1,000 ml. and 1,500 ml. with inflow and outflow rates being 350 ml. per minute. A continous, alternate, sequential inflow and outflow was utilized so that there was continuous fluid flow into or out of the peritoneal cavity throughout the dialysis process.

The patient exhibited urea clearances of about 29 to 39 ml. of urea and about 26 to 35 ml. of creatinine in these various peritoneal dialysis operations at the varying IPV and stroke volumes. Ultrafiltration was also quite controllable and adequate.

It has also been found that using this technique plus a peritoneal dialysis catheter implanted under the skin as described in the co-pending application titled Peritoneal Dialysis Catheter filed concurrently herewith, that a very low infection rate (0.7%) has been encountered very substantially below the 2 to 3 percent peritonitis rate, which is encountered in peritoneal dialysis procedures using "hanging bottles."

It is preferred for the dialysis solution which has been removed from the peritoneal cavity to be, in turn, dialyzed against a second dialysis solution for removal of metabolic waste products therefrom. The removed peritoneal dialysis solution is thereafter returned in a flow circuit to the peritoneal cavity of a patient as a relatively fresh dialysis solution.

Also, a single access path to the abdominal wall to the peritoneum is preferably utilized to both insert and remove dialysis solution to and from the peritoneal cavity.

A peritoneal dialysis apparatus used herein comprises a container for holding dialysis solution, means for connection with the peritoneal cavity, and conduit means for connecting the container and the connection means. Pump means are provided for alternatingly pumping dialysis solution in opposite directions between the container and the peritoneal cavity. Also, means for purifying the dialysis solution removed from the peritoneal cavity are provided prior to reinsertion thereof into the peritoneal cavity. This purification means can be a dialyzer as indicated.

Figure 1:
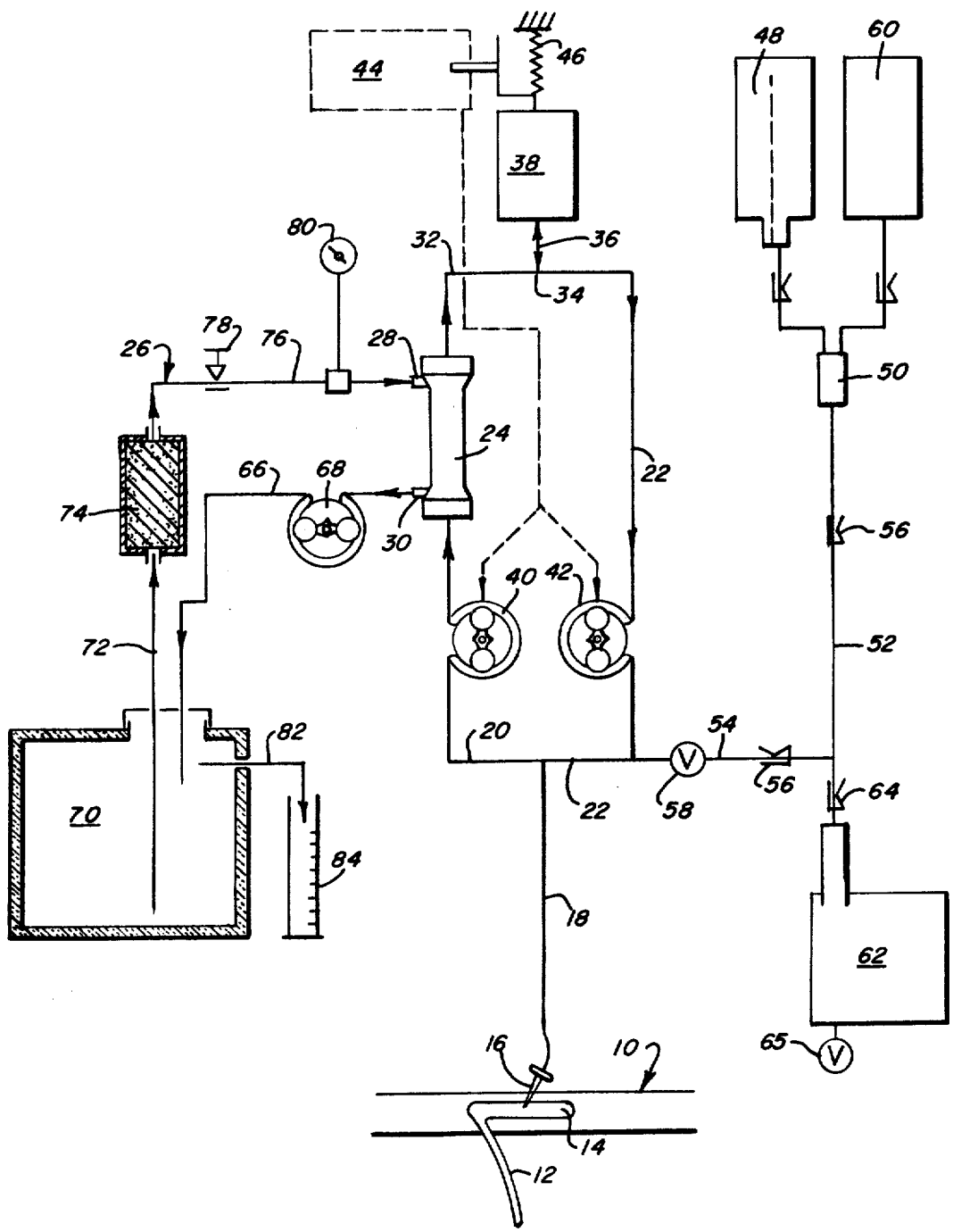
FIG. 1 is a schematic diagram of a peritoneal dialysis system, utilizing the method and apparatus of this invention.

In the drawings, FIG. 1 shows a peritoneal dialysis system for automatically practicing the method of this application.

The abdomen of a patient 10 is schematically represented, having emplaced therein a permanent peritoneal dialysis catheter 12, extending into the peritoneum and having an enlarged portion 14 under the skin of the patient for periodic access by a cannula 16 when peritoneal dialysis is to be accomplished.

As stated above, this catheter is described in the copending application of Willem Kolff et al, Ser. No. 828,019 filed Aug. 26, 1977 on even date herewith.

Cannula 16 is connected to tubing 18 which in turn connects to the junction of two lines 20, 22. Line 20 communicates at its other end with a dialyzer 24, which serves as means for purifying dialysis solution removed from the peritoneal cavity. A suitable dialyzer for use herein may be the CF$^{TM}$ Hollow Fiber Dialyzer, available from Travenol Laboratories, Inc. of Deerfield, Illinois.

Dialysis solution for dialyzing the peritoneal dialysis solution is provided by dialysis system 26 into dialysis solution inlet 28 and outlet 30 of dialyzer 24.

The purified dialysis solution passing from dialyzer 24 is carried by flow conduit 32 to another Y-junction 34, one of the legs of which is a conduit 36, communicating with reservoir 38 for holding dialysis solution. Reservoir 38 may be a conventional sterile plastic solution bag capable of expanding to hold a variable volume of dialysis solution.

The other leg of the Y-junction 34 is conduit 22, which communicates with tubing 18. A pair of roller pumps 40, 42 are provided for alternative operation by control system 44.

Weight-sensitive switching mechanism 46 is provided for operation of control system 44. Reservoir 38 is suspended from switching mechanism 46 so that the control system 44 operates pumps 40, 42 in a manner responsive to the weight of peritoneal dialysis solution in reservoir 38.

In operation of this part of the system of this invention, peritoneal dialysis solution in the amount of, for example, 1,500 ml., is initially administered to the patient from container 48, which may be a bottle or a sterile parenteral solution bag as desired. The solution passes through Y-connection 50, and then through flow line 52, 54 equipped with clamps 56. Also valve 58 may be provided if desired.

Container 60 may be provided for normal saline solution to wash out the peritoneal cavity at the termination of dialysis. Drain bag 62, equipped with on-off clamp 64 and a drain valve 65, may be provided for receiving the peritoneal drainage at the end of the process.

Accordingly, the IPV of solution is administered from container 48 to peritoneal cavity 10. Following this, reservoir bag 38 being empty, control system 44 actuates pump 40 to begin to withdraw the stroke volume, which is a predetermined fraction of the IPV (for example 40 percent) from the peritoneal cavity. This withdrawn solution passes through dialyzer 24, and is accordingly purified, then passing through conduit 32 and into reservoir 38, since roller pump 42 is inactive and positioned to block flow through line 22.

Accordingly, as outflow from the peritoneal cavity, through dialyzer 24 to reservoir 38 takes place, typically on the order of a rate of 350 ml. per minute, reservoir 38 increases in weight, stretching spring 46. When the weight reaches a predetermined amount, switch 46 and control system 44 act to shut off pump 40 and to actuate roller pump 42, which results in the draining of the regenerated peritoneal dialysis solution from reservoir 38 through conduits 22 and 18 back into the peritoneal cavity.

When bag 38 reaches a predetermined minimum weight, another limit switch is actuated in switch system 46 to cause control unit 44 to shut off pump 42 and again to reactivate pump 40.

This process continues with alternate filling and draining of the peritoneal cavity to achieve the method of this invention with its improved characteristics.

Dialyzer system 26 comprises dialysis solution outlet line 66 connected to outlet 30 of the dialyzer, through which flow is impelled by roller pump 68. Line 66 leads to reservoir 70 for dialysis solution, from which another line 72 passes, being connected to sorbent cartridge 74, which may contain charcoal or the like. Line 76 then communicates between charcoal cartridge 74, passing by an emergency shut-off valve 78 and pressure monitor 80, and finally communicating with inlet 28 of the dialyzer 24.

Horizontal outlet 82 can be used as shown to directly measure ultrafiltration since water of ultrafiltration passing into the peritoneal dialysis solution will be extracted by dialyzer 24, and accordingly will increase the solution volume in circuit 26. This increased solution volume will result in an increase in the liquid level in chamber 70, causing a spillover through line 82 into burette 84, where it may be measured. The ultrafiltration volume of liquid removed generally is not counted in the stroke volume, since it does not reach reservoir 38. Instead, it is removed through dialyzer 24.

Control means 44 includes an electrical control circuit, while switching mechanism 46 may be mechanical.

Figure 2:
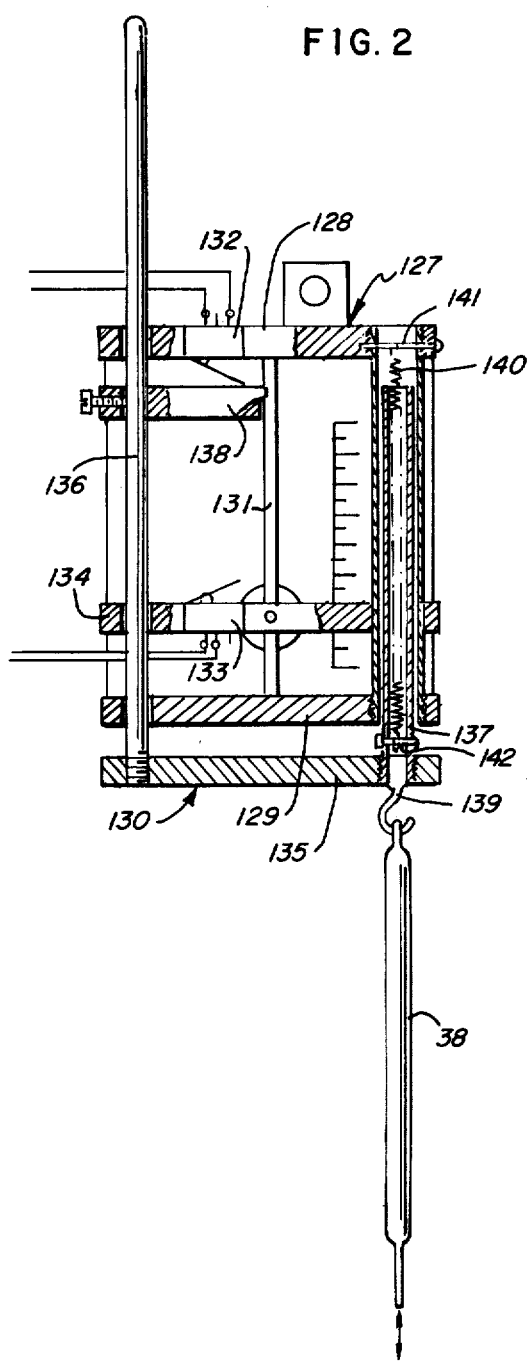
FIG. 2 is a cross section of the mechanical switching mechanism in its configuration when the reservoir for holding dialysis solution is empty.
Figure 3:
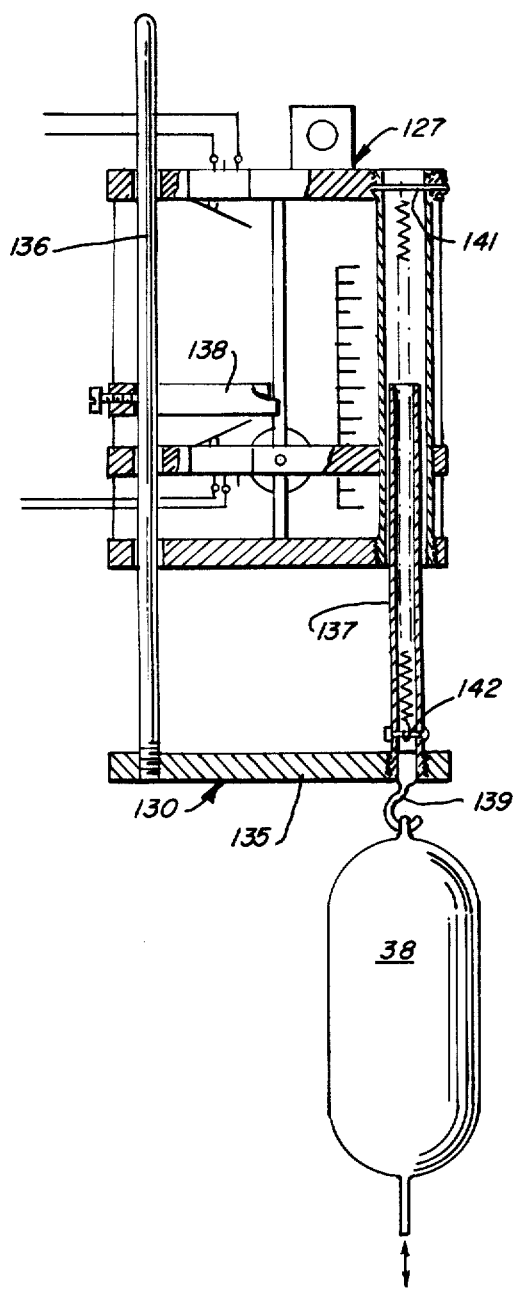
FIG. 3 is a cross section of a mechanical switching mechanism in its configuration when the reservoir for holding dialysis solution is full.

As illustrated in FIG. 2, the mechanical switching means includes a stationary bracket 127 which carries movable bracket 130. The stationary bracket 127 has an upper plate 128 and a lower plate 129 connected together by guide rod 131. Two switches are carried by the bracket 127: one switch 132 for starting the inlet pump 42 and for stopping the outlet pump 40, and another switch 133 for reversing the operation of these pumps. In the preferred embodiment, outflow switch 132 is secured to bracket 127, and inflow switch 133 is secured to switch-holding member 134. The switch-holding member 134 is adjustably fixed to guide rod 131. Movable bracket 130 is comprised of a horizontal arm 135 and vertical shafts 136 secured at one end of the arm, with a vertical hollow cylinder 137 secured at the other end of the arm and parallel to the shaft 136. The bracket 127 defines openings through plates 129, 134, and 128 to allow vertical movement of the shaft 136 and the cylinder 137 therethrough without substantial interference. Secured to shaft 136 is a switch-trip member 138. The trip member 138 is secured to the shaft by an adjustable set screw which allows it to be set at a predetermined position on the shaft. The horizontal arm 135 supports a hook 139 for carrying the reservoir bag 38. A spring 140 is fixed to pin 141 in plate 128 and pin 142 in cylinder 137.

With this apparatus, as reservoir 38 is filled with dialysis solution pumped out of the patient, the increasing weight will cause the spring 140 to extend, allowing the movable bracket 130 to move downwardly relative to the stationary bracket 122. Once the bag has been filled to an amount equal to the stroke volume, the spring will extend to such an extent that the trip member 138 will engage and operate inflow pump switch 133. This causes pump 42 to start and pump 40 to stop, so that the fluid in reservoir 38 is pumped out of the bag and into the patient.

When reservoir 38 becomes depleted, the spring 140 shortens, allowing the movable bracket 130 to move toward engagement with the stationary bracket 122. As the bag becomes substantially completely depleted, the switch trip member 138 engages the outflow pump switch 132 at the top of the plate 22. This reverses the pump operation causing the outflow pump 40 to pump fluid into the bag, and stopping the inflow pump 42, to withdraw peritoneal dialysis solution into reservoir 38. This cycled operation continues until the system is shut down by the patient.

Figure 4:
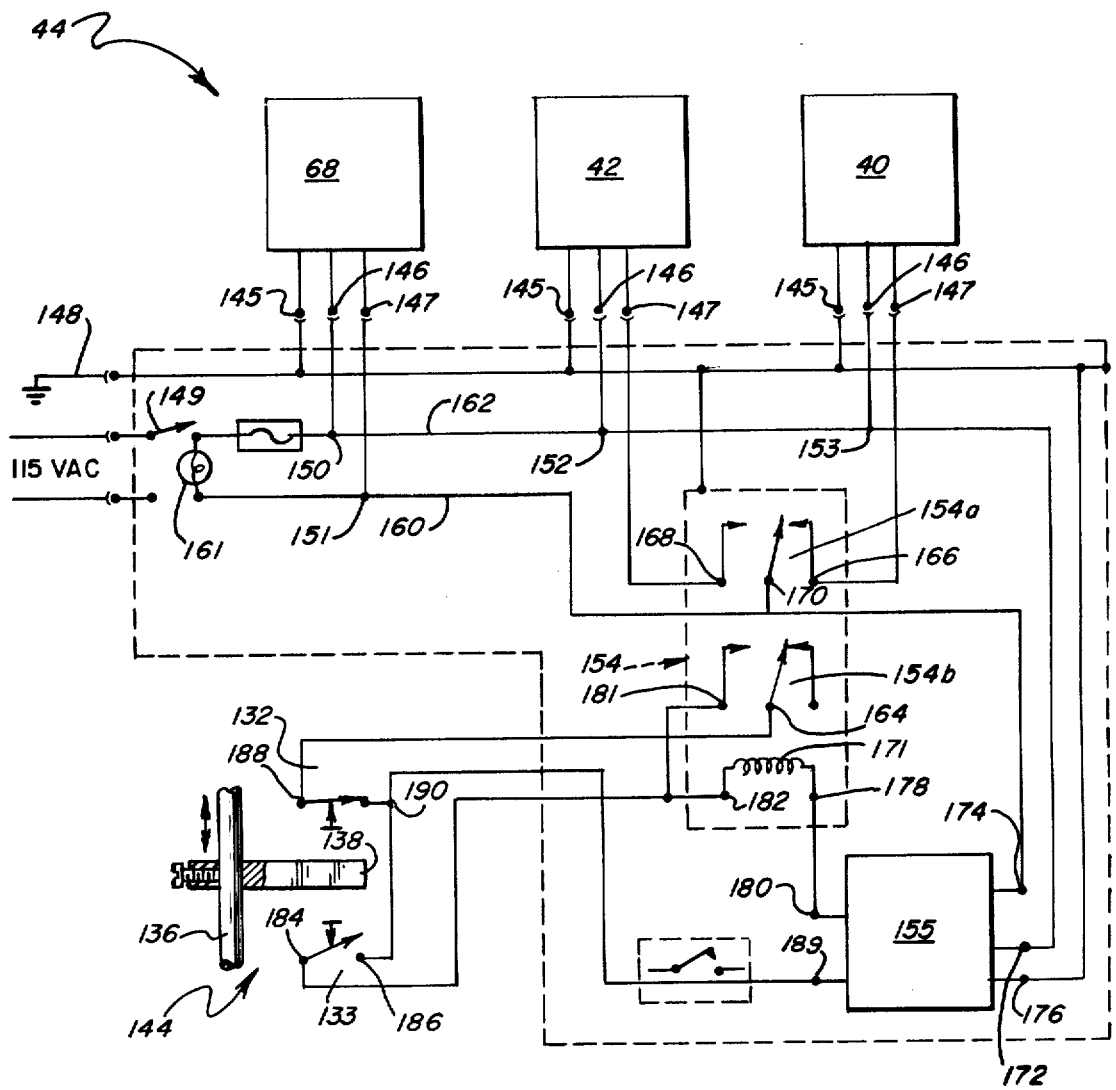
FIG. 4 is a schematic diagram of a control circuit for the switching mechanism shown in FIGS. 2 and 3.

The control circuit 44 for controlling the flow of fluid is shown schematically in FIG. 4. This circuit controls pumps 40, 42, and 68, and includes a switch 144 for controlling the operation of the pumps in a desired manner. Each of the pumps 40, 42, 68 have a ground terminal 145, and input power terminals 146 and 147. The control circuit 44 also includes a common ground line 148. A line 160 is connected to a 115 volt alternating-current power source. A line 162 is connected through a main power switch 149 to the alternating-current power source. An indicating lamp 161 is connected across lines 160 and 162 to indicated when the power is "on".

The terminal 146 of the dialyzer pump 68 is connected to line 162 at terminal 150. The terminal 147 of dialyzer pump 68 is connected to line 160 at a terminal 151.

The terminals 146 of pumps 40 42 are connected to line 162 through terminals 152, 153, respectively. The first section 154a of a double-pole, double-throw, relay 154 is connected to energize or de-energize pumps 40, 42 in a predetermined sequence. Relay 154 has an arm 170 and a pair of contacts 166, 168. Terminal 147 of pumps 40, 42 are connected to contacts 168, 166, respectively of relay 154, while relay arm 170 is connected to line 160. In the unenergized position, arm 170 of relay 154 normally engages contact 166 which results in the outlet pump 40 being placed in the operative mode. When the relay 154 is energized, arm 170 engages contact 168 causing the inlet pump 42 to operate and the outlet pump cease operating.

As discussed below, the coil 171 of relay 154 is energized by a full-wave rectifier 155 through switch 144. Switch 144 comprises inflow pump switch 133 and outflow pump switch 132. The input terminals 172, 174 of the rectifier 155 are connected to lines 162, 160 respectively, and the ground terminal 176 of the rectifier is connected to the ground line 148. One of the terminals 178 of the relay coil is connected to one of the output terminals 180 of the rectifier, and the other terminal 182 of the relay coil is connected to arm 184 of the normally open inflow pump switch 133. Terminal 186 of the normally open switch 133 is connected to the ground output terminal 188 of the rectifier 155. When switch 133 is closed, the relay will become energized to move the arms 164, 170 of relay 154. With regard to the first section 154a of the relay, this has the effect of connecting the inflow pump 42 into the circuit, thereby into operation, and disconnecting the outflow pump 40.

The second section 154b of the relay 154 is controlled by the relay coil to hold the relay coil energized after the trip member 138 has disengaged the normally open inflow pump switch 133. The contact 181 of the second section of the relay is connected to terminal 182 of the relay coil. Arm 164 of the second section of the relay is connected to arm 188 of the normally closed outflow pump switch 132, and switch terminal 190 of switch 132 is connected to switch terminal 186 of inflow pump switch 133 and terminal 188 of the full wave rectifier. With this configuration, once the relay coil is energized, a connection between contact 181 and terminal 188 will be made to complete a circuit which will hold the relay coil in an energized condition until de-energized by the opening of the normally closed outflow pump switch 132. At that point, the relay coil will become de-energized allowing the relay arms 170, 164 to revert to their normal position. This has the effect of disconnecting the inflow pump from the circuit and connecting the outflow pump to put it into operation.

In summary, the control circuit causes the inflow pump 42 to begin operation upon closure of the normally open inflow pump switch 133 by the trip member 138 and simultaneously stops operation of the outflow pump 40. The reverse occurs upon the opening of the normally closed outflow pump switch 132. This circuit allows each pump to remain in operation with its counterpart inoperative until the switch of the counterpart is actuated.

Figure 5:
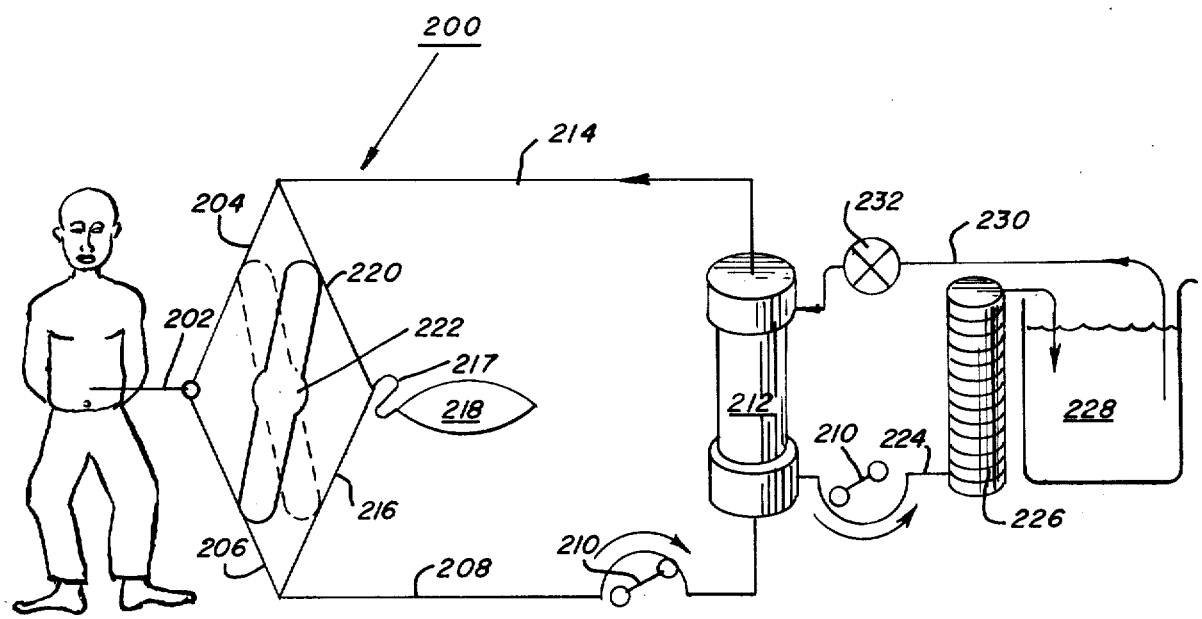
FIG. 5 is a schematic diagram of another embodiment of the method and apparatus of this invention.
Figure 6:
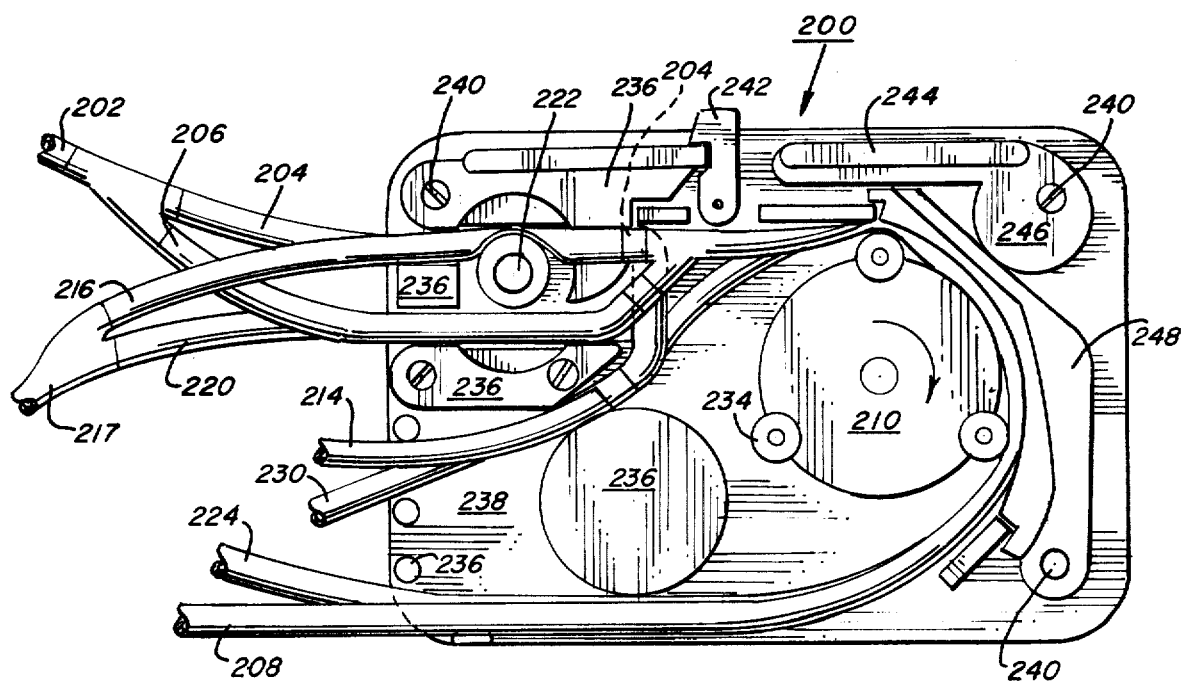
FIG. 6 is a plan view of the roller pump utilized in FIG. 5, also showing the pattern of flow conduits through it.

Referring now to FIGS. 5 and 6, an alternate flow system 200 for practicing the invention of this method is disclosed. A connection conduit 202 is provided to a patient, terminating in a Y-junction with branch conduits 204 and 206, which comprise first and second conduits positioned in branched relationship with the connection conduit. A primary circuit line 208 connects with conduit 206, and leads through an appropriate pump 210, such as a roller pump, communicating with a dialyzer 212. Return line 214 communicates with branch conduit 204 to complete one circuit.

Third branched conduit 216 communicates in a Y-connection with the junction of conduits 206, 208 at one end, and communicates with a line communicating with reservoir 218 at its other end.

Fourth conduit 220 is positioned in branched relation with third conduit 216 and the line leading to reservoir 218 at one end, and in Y-connection with second conduit 204 and return line 214 at its other end.

A valve 222 is schematically shown (in FIG. 5) to be capable of alternatively opening and closing fluid flow through pairs of the branch conduits. The pairs of branch conduits comprise, respectively, the first and fourth branch conduits 206, 220 and the second and third branch conduits 204, 216, with valve 222 being adapted so that flow of dialysis solution takes place through only one pair of branch conduits at a time on an alternative basis.

Thus, when valve 222 is in a first position to block branch conduits 204 and 216, the withdrawal of dialysis solution from the peritoneal cavity takes place through branch conduit 206, and primary circuit lines 208 and 214, passing then through branch conduit 220 to reservoir 218.

When valve 222 is in its opposite position, blocking branch conduits 206 and 220, the flow of dialysis solution is from the reservoir 218, through branch conduit 216, through primary circuit lines 208 and 214, and then through branch conduit 204 into connection line 202 for readministration to the peritoneal cavity. Accordingly, the alternative flow into and out of the peritoneal cavity in accordance with this invention is accomplished.

Dialyzer 212 is connected to an outlet line 224, which also passes through the same pump 210 as line 208 does. Pump 210 is shown twice in the schematic drawing of FIG. 5 for ease of understanding the system of flow, while an actual arrangement of the lines passing through pump 210 is shown in FIG. 6.

Thereafter, the dialysis solution may pass through a charcoal column or other sorbent 226, which, in turn, has a conduit leading to dialyzate storage tank 228, which may preferably be of about 60 liters capacity. A return line 230 is provided, leading from the dialyzate tank to the dialysis solution inlet of the dialyzer. An ultrafiltration regulation valve 232 of conventional design may also be provided in this circuit as shown.

One advantage of this system is that the peritoneal dialysis solution is dialyzed twice prior to readministration: once upon removal from the peritoneal cavity while travelling to reservoir 218, and once upon passage from the reservoir back to the peritoneal cavity.

Referring particularly to FIG. 6, an actual embodiment of valve 222 is shown to be an eccentrically positioned rotating member, adapted to shut off flow in either lines 206, 220 or to lines 204, 216. While the embodiment of FIG. 6 represents the actual appearance of an embodiment used in this invention, the flow conduits and their function are the same as the schematic FIG. 5.

Roller pump 210 can be seen to comprise a plurality of satellite rollers 234 as shown. Also, there are various guide members 236 and the like, to permit installation of the branched tubing which comprises the various lines utilized herein, so that they may be positioned in appropriate relation to the rotating valve member 222, and so that the pair of lines 208, 224 may be pumped by the single roller pump 210.

For convenience of operation and installation, some of the guide members 236 are attached in hinged relationship to the frame 238 of the roller pump valving member shown in FIG. 6, being attached by hinges 240 so that they may swing outwardly for installation and removal of the various flow lines. Latch 242 is provided on one member 236, while another member defines a handle 244 so that it may be manually swung outwardly, to move off-center lug 246 out of the way to permit the opening of retainer member 248 about the roller pump.

Dialyzer 212 and reservoir 218 are not shown in FIG. 6, but the connection conduits 208 and 217 leading to them are seen.

The above has been offered for illustrative purposes only, and is not for the purpose of limiting the invention of this application, which is as defined in the claims below.

That which is claimed is:

1. A method of removing metabolic waste products from the blood of a patient including pumping dialysis solution into the peritoneal cavity of the patient, the improvement comprising (a) removing a portion of the dialysis solution from the peritoneal cavity through a single access path in the abdominal wall to the peritoneum to both insert and remove dialysis solution to and from the peritoneal cavity which portion is no more than essentially 90 percent of the total amount of dialysis solution administered to said peritoneal cavity, (b) replacing said portion with additional, fresh dialysis solution, sequentially repeating steps (a) and (b) until the desired amount of metabolic waste products have been removed from the patient, (c) dialyzing said dialysis solution which has been removed from the peritoneal cavity against a second dialysis solution for removal of metabolic waste products therefrom, (d) returning said removed dialysis solution to the peritoneal cavity of the patient as cleansed dialysis solution, (e) passing said second dialysis solution through absorbent means to regenerate said second dialysis solution for further dialysis against the dialysis solution removed from the peritoneal cavity, (f) directing said dialysis solution into and out of the peritoneal cavity in the manner responsive to the weight of dialysis solution in a reservoir positioned in flow communication with the peritoneal cavity, flowing said dialysis solution into and out of the peritoneal cavity of a patient through a flow circuit which defines communication means with said catheter, (g) providing first and second branch conduits positioned in branched relationship with said connection means, a primary circuit having one end connected to said first conduit and another end connected to said second conduit, said primary circuit passing through pump means and dialyzer means for purification of the solution, said first branch conduit communicating with a third branch conduit, upstream of said pump, which in turn communicates with a reservoir for dialysis solution, said second branch conduit being in flow communication with a fourth branch conduit, said fourth branch conduit also communicating with said reservoir; and valve means for alternatively opening and closing fluid flow through pairs of branch conduits, said pairs of branch conduits comprising respectively the first and fourth and the second and third branch conduits, whereby flow of dialysis solution takes place through only one pair of said branch conduits on an alternative basis, to permit the withdrawal of dialysis solution from the peritoneal cavity and the storage thereof in said container when the second and third branch conduits are open, and to permit the reinfusion of dialysis solution from the container to the peritoneal cavity when the first and fourth branch conduits are open.

2. The method of claim 1 in which from 1,000 to 2,500 ml. of dialysis solution is initially inserted into the peritoneal cavity, and thereafter, aliquots of 500 to 1,500 ml. of said solution are removed from the peritoneal cavity for purification and reinsertion.

3. The method of claim 2 in which aliquots of dialysis solution are removed and reinserted to the peritoneal cavity at least five times during the course of treatment.

4. The method according to claim 3 in which dialysis solution is passed to and from the peritoneal cavity via a catheter implanted under the skin of the patient having a portion thereof extending into the peritoneal cavity.

5. Peritoneal dialysis apparatus for removing metabolic waste products from the blood of a patient including a means for pumping dialysis solution into the peritoneal cavity of the patient, the improvement comprising: (a) means for removing a portion of the dialysis solution from the peritoneal cavity, which portion is no more than essentially 90 percent of the total amount of dialysis solution administered to said peritoneal cavity; (b) means for replacing said portion with additional, fresh dialysis solution, sequentially repeating steps (a) and (b) until the desired amount of metabolic waste products have been removed from the patient, said removing means comprising conduit means including a connection member for communication with a peritoneal dialysis catheter inserted in the peritoneal cavity, first and second branch lines connected to said connection member in branched connection therewith, pump means for actuating flow through said first and second branch lines; said dialyzer being positioned in said first branch line, said first and second branch lines communicating with said reservoir, said pump means being adapted to alternatingly provide dialysis solution flow from said connection member through the first branch line and the dialyzer to the reservoir, and flow from said reservoir to said connection member through said second branch line, and control means, actuated by the weight of dialysis solution in said reservoir to alternatingly cause flow through said first line to fill said reservoir when the reservoir is of a predetermined minimum weight and to cause flow through said second branch line from said reservoir to the peritoneal cavity when the reservoir is of a predetermined maximum weight; sorbent means for a second dialysis solution in a second circulating flow path passing through said dialyzer for dialytic exchange with the dialysis solution which is circulated to and from the peritoneal cavity; and switching means operable by the weight of said reservoir including a spring, an outflow switch connected to said pump means to initiate flow through said first branch line and an inflow switch connected to said pump means to control flow through said second branch line, said reservoir being connected to one end of the spring, and a trip member connected to said spring, whereby as said container is filled with dialysis solution to a predetermined amount, it stretches the spring, causing the trip member to trip said outflow switch for terminating flow through the second branch line to empty said reservoir and to fill the peritoneal dialysis cavity, and further whereby as said reservoir is emptied, said spring contracts to cause the trip member to actuate said inflow switch to terminate flow through said second branch line and to initiate flow through the first branch line for causing flow out of the peritoneal cavity and into said reservoir.

6. The apparatus according to claim 5 which includes first and second branch conduits positioned in branched relationship with said means for connection with the peritoneal cavity, a primary circuit having one end connected to said first conduit and another end connected to said second conduit, said primary circuit passing through pump means and dialyzer means for purification of the solution, said first branch conduit in communication with a third branch conduit, upstream of said pump, which in turn communicates with a reservoir for dialysis solution, said second branch conduit being in flow communication with a fourth branch conduit, said fourth branch conduit also communicating with said reservoir; and valve means for alternatively opening and closing fluid flow through pairs of branch conduits, said pairs of branch conduits comprising respectively the first and fourth and second and third branch conduits, whereby flow of dialysis solution takes place through only one pair of said branch conduits on an alternative basis, to permit the withdrawal of dialysis solution from the peritoneal cavity and the storage thereof in said container when the second and third branch conduits are open, and to permit the reinfusion of dialysis solution from the container to the peritoneal cavity when the first and fourth branch conduits are open.

7. The apparatus of claim 6 in which said means for purifying the dialysis solution is a dialyzer for the dialysis solution.

8. The apparatus according to claim 7 in which said dialyzer is equipped with sorbent means for a second dialysis solution in a second circulating flow path passing through said dialyzer for dialytic exchange with the dialysis solution which is circulated to and from the peritoneal cavity.

9. The apparatus of claim 8 in which said valve means for alternatively opening and closing fluid flow through the pairs of branch conduits is responsive to means for sensing the volume of dialysis solution in said container for holding dialysis solution, to selectively open and close said branch conduits to permit the withdrawal of dialysis solution from the peritoneal cavity when the container has a predetermined minimum amount of dialysis solution, and to permit the reinfusion of dialysis solution from the container when the container has a predetermined maximum amount of dialysis solution therein.

10. The apparatus of claim 9 in which a single roller pump is used to propel peritoneal dialysis solution through said primary circuit and branch conduits, and also to propel dialysis solution in a dialyzer circuit for purification of the peritoneal dialysis solution.

11. The apparatus of claim 10 in which said valve means for alternatively opening and closing fluid flow through pairs of branched conduits comprises an eccentrically rotatable member to respectively press against pairs of flexible tubes comprising said branched connections, to shut off flow through said one pair and then said other pair as said eccentric member rotates.

* * * * *